United States Patent [19]

DeMarinis et al.

[11] Patent Number: 4,686,218

[45] Date of Patent: Aug. 11, 1987

[54] USE OF 6-CHLORO-3-METHYL-1H-2,3,4,5-TETRAHYDRO-3-BENZAZEPINE-N-OXIDE, AS A PRODRUG

[75] Inventors: Robert M. DeMarinis, Ardmore; Kenneth M. Straub, Philadelphia, both of Pa.

[73] Assignee: SmithKline Beckman Corporation, Philadelphia, Pa.

[21] Appl. No.: 696,377

[22] Filed: Jan. 30, 1985

[51] Int. Cl.$^4$ .............................................. A61K 31/55
[52] U.S. Cl. .................................. 514/213; 540/594
[58] Field of Search ................ 560/239 BB; 514/213; 540/594

[56] References Cited

U.S. PATENT DOCUMENTS

| 3,496,166 | 2/1970 | Mull et al. ................. 260/239 BB |
| 3,752,892 | 8/1973 | Hoegerle et al. ............ 260/239 BB |
| 4,465,677 | 8/1984 | DeMarinis et al. ................ 540/594 |

OTHER PUBLICATIONS

Staube et al., Jun. 1, 1984, 32nd Annual Conference on Mass Spectrometry and Allied Topics (pp. 785–786).

*Primary Examiner*—Glennon H. Hollrah
*Assistant Examiner*—D. B. Springer
*Attorney, Agent, or Firm*—Joseph A. Marlino; Stuart R. Suter; Alan D. Lourie

[57] ABSTRACT

6-Chloro-3-methyl-1H-2,3,4,5-tetrahydro-3-benzazepine-N-oxide is prepared by mild oxidation of the corresponding amine. It has been found to have prolonged $\alpha_2$-antagonistic or antihypertensive activity.

4 Claims, No Drawings

USE OF 6-CHLORO-3-METHYL-1H-2,3,4,5-TETRAHYDRO-3-BENZAZEPINE-N-OXIDE, AS A PRODRUG

This invention relates to 6-chloro-3-methyl-1H-2,3,4,5-tetrahydro-3-benzazepine-N-oxide and its use as an anti-hypertensive agent.

BACKGROUND OF THE INVENTION

Certain N-substituted-1H-2,3,4,5-tetrahydro-3-benzazepines are described in U.S. Pat. No. 4,465,677 to have alpha$_2$ antagonistic activity which is of benefit in treating abnormal cardiovascular conditions such as hypertension. The leading species described there is the 3-methyl-6-chloro congener. This compound, as noted at column 1 in the Description of Prior Art of the reference patent, had previously been reported to be used as a chemical intermediate.

The N-oxide of 6-chloro-3-methyl-1H-2,3,4,5-tetrahydro-3-benzazepine was detected in urine as a metabolite of the parent amine in rats. This work was described in a paper presented on June 1, 1984 at the 32nd Annual Conference on Mass Spectrometry and Allied Topics. No utility was described for the N-oxide species in that paper.

DESCRIPTION OF THE INVENTION

We have now confirmed that from 35–40% of 6-chloro-3-methyl-1H-2,3,4,5-tetrahydro-3-benzazepine, following administration to humans, is converted to the N-oxide of this invention and excreted as such in the urine.

6-Chloro-3-methyl-1H-2,3,4,5-tetrahydro-3-benzazepine-N-oxide is prepared by mild oxidation of the corresponding amine, such as using m-chloroperbenzoic acid in methylene chloride at room temperature. The product is isolated by standard chemical methods.

6-Chloro-3-methyl-1H-2,3,4,5-tetrahydro-3-benzazepine-N-oxide proved to be inactive in standard in vitro pharmacological tests for $\alpha_2$-antagonist activity, such as in the isolated guinea pig atrium protocol. The parent amine, on the contrary, was very active in this test (column 3, lines 20–23 of U.S. Pat. No. 4,465,677).

One skilled in the art often expects a metabolic product of a medicinal agent to be inactive since conversion of a biologically active compound to a metabolite is a function of the excretion sequence. When the N-oxide was found to be inactive in vitro, the presumption that the compound would have no useful $\alpha_2$-antagonistic activity was believed to have been confirmed.

We have now discovered that, when 6-chloro-3-methyl-1H-2,3,4,5-tetrahydro-3-benzazepine-N-oxide is administered internally to hypertensive animals, it demonstrates a potent, long-lasting biological effect. For example, the N-oxide of this invention, 25 mg/kg administered orally to spontaneously hypertensive rats in the protocol described in column 3 of U.S. Pat. No. 4,465,677, lowers blood pressure by 50–60 mm/kg, with the effect lasting several hours. We believe, therefore, that this new compound acts as a prodrug for the parent compound, whose utility is descirbed in the patent cited above, but with a delayed and prolonged course of action.

The pharmaceutical compositions used to carry out the method of producing alpha$_2$ antagonism and anti-hypertensive activity of this invention comprise a pharmaceutical carrier and, as the active ingredient, 6-chloro-3-methyl-1H-2,3,4,5-tetrahydro-3-benzazepine-N-oxide. The active ingredient will be present in the compositions in an effective amount to produce alpha$_2$ antagonism and antihypertensive activity.

Preferably, the compositions contain the active ingredient in an amount of from about 25 mg to about 200 mg, advantageously from about 50 to about 125 mg, per dosage unit.

The pharmaceutical carrier may be for example a solid or a liquid. Exemplarly of solid carriers are lactose, magnesium stearate, terra alba, sucrose, talc, stearic acid, gelatin, agar, pectin or acacia. The amount of solid carrier will vary widely but preferably will be from about 25 mg to about 1 gm. Exemplary of liquid carriers are syrup, peanut oil, olive oil, sesame oil, propylene glycol, polyethylene glycol and water. The carrier or diluent may include a time delay material well known to the art such as, for example, a glyceryl or cellulose ester or ether.

A wide variety of pharmaceutical forms can be employed, for example, the preparation may take the form, of tablets, capsules, powders, troches, patches, lozenges, syrups, emulsions, sterile injectable liquids or oral liquid suspensions or solutions. Dosage unit forms adapted for oral administration are preferred.

The pharmaceutical compositions are prepared by conventional techniques involving procedures such as mixing, granulating and compressing or dissolving the ingredients as appropriate to the desired preparation.

The method of producing alpha$_2$ antagonism, which is manifested as an antihypertensive effect according to this invention, comprises administering internally to a needful human or animal patient a quantity of the benzazepine N-oxide of this invention sufficient to produce such activity without toxic side effects.

Preferably, the N-oxide compound is administered in conventional dosage unit forms prepared by combining an appropriate dose of the compound with standard pharmaceutical carriers.

The active ingredient will be administered internally in a daily dosage regimen of N-oxide selected from about 50 mg to about 500 mg, most preferably from about 75 mg to about 200 mg. Advantageously, equal doses will be administered one to two times per day orally. When the administration is carried out as described above, alpha$_2$ antagonism and anti-hypertensive activity are produced.

The route of administration of the pharmaceutical compositions of this invention and in accordance with the methods of this invention is internal, either parenteral or preferably oral, in an amount to produce the desired biological activity without side-effects. Parenteral administration will employ dosage units and daily dosage regimens roughly one half those disclosed above which are aimed at the preferred oral routes of administration.

The following examples are not limiting but are illustrative of this invention. The temperatures are in degrees Centigrade.

EXAMPLE 1

A solution of 2.5 g (12.9 mmol) of 6-chloro-3-methyl-1H-2,3,4,5-tetrahydro-3-benzazepine in 25 ml of methylene chloride was treated dropwise with a solution of 2.6 g (15 mmol) of meta-chloroperbenzoic acid in 20 ml of methylene chloride. After addition had been completed, the mixture was stirred at room temperature for two hours. The reaction was evaporated to a solid residue, dissolved in a small amount of chloroform/methanol (3:1) and filtered through a short column of basic alumina, eluting with chloroform/methanol (3:1). The filtrate was evaporated to a white solid which was triturated with ether and filtered to give 2.2 g of white crystals, mp 178°–180°, of 6-chloro-3-methyl-1H-2,3,4,5-tetrahydro 3-benzazepine N-oxide.

Anal. for $C_{11}H_{14}ClNO \cdot H_2O$: Calcd. C, 57.52; H, 6.90; N, 6.11. Found: C, 57.52; H, 7.02; N. 6.10.

EXAMPLE 2

| Ingredients | Amounts |
|---|---|
| 6-Chloro-1H—2,3,4,5-tetrahydro-3-methyl-3-benzazepine-N—oxide | 100 mg |
| Lactose | 400 mg |

The ingredients are mixed and filled into a hard gelatin capsule.

One capsule is administered twice a day orally to a hypertensive patient.

EXAMPLE 3

| Ingredients | Amounts |
|---|---|
| 6-Chloro-1H—2,3,4,5-tetrahydro-3-methyl-benzazepine-N—oxide | 150 mg |
| Calcium sulfate dihydrate | 200 mg |
| Sucrose | 25 mg |
| Starch | 15 mg |
| Talc | 5 mg |
| Stearic Acid | 3 mg |

The calcium sulfate dihydrate, sucrose and the N-oxide are thoroughly mixed and granulated with 10% gelatin solution. The wet granules are screened, dried and then mixed with the starch, talc and stearic acid, screened and compressed into a tablet.

One tablet is administered once a day orally to a patient in need of extended $\alpha_2$-antagonistic activity.

What is claimed is:

1. A method of producing $\alpha_2$-antagonistic activity in a patient in need thereof comprising administering internally to said patient an effective therefor, nontoxic quantity of 6-Chloro-3-methyl-1H-2,3,4,5-tetrahydro-3-benzazepine-N-oxide as a prodrug.

2. The method of claim 1 in which the patient is hypertensive.

3. The method of claim 1 in which a dosage unit selected from the range of from 25–200 mg of said compound is administered orally.

4. The method of claim 2 in which a dosage unit selected from the range of from 50–125 of said compound is administered orally once or twice daily.

* * * * *